United States Patent [19]

Nakagawa et al.

[11] Patent Number: 5,343,733
[45] Date of Patent: Sep. 6, 1994

[54] ABRASION TESTING METHOD

[75] Inventors: Mitsuhiko Nakagawa; Shiro Nakajima, both of Itami, Japan

[73] Assignee: Sumitomo Electric Industries, Ltd., Osaka, Japan

[21] Appl. No.: 827,709

[22] Filed: Jan. 27, 1992

[30] Foreign Application Priority Data

Jan. 30, 1991 [JP] Japan .................. 3-009581

[51] Int. Cl.$^5$ .............................................. G01N 3/56
[52] U.S. Cl. ............................................ 73/7; 73/121
[58] Field of Search ................... 73/7, 8, 9, 10, 121

[56] References Cited

U.S. PATENT DOCUMENTS

| | | | |
|---|---|---|---|
| 1,444,803 | 2/1923 | Ratner et al. | 73/7 |
| 2,981,929 | 4/1961 | Rizzo et al. | 73/7 X |
| 3,360,977 | 1/1968 | Herman | 73/7 X |
| 3,648,121 | 3/1972 | Groat et al. | 73/9 |

FOREIGN PATENT DOCUMENTS

| | | |
|---|---|---|
| 0214687 | 3/1987 | European Pat. Off. . |
| 2849203 | 11/1979 | Fed. Rep. of Germany ............ 73/7 |
| 3007887 | 9/1981 | Fed. Rep. of Germany . |
| 3640700 | 6/1988 | Fed. Rep. of Germany ............ 73/7 |
| 3816949 | 12/1988 | Fed. Rep. of Germany . |
| 102433 | 4/1990 | Japan .................................. 73/7 |
| 998919 | 2/1983 | U.S.S.R. .............................. 73/7 |
| 1244561 | 7/1986 | U.S.S.R. .............................. 73/7 |
| 1298609 | 3/1987 | U.S.S.R. .............................. 73/7 |

Primary Examiner—Tom Noland
Attorney, Agent, or Firm—Wenderoth, Lind & Ponack

[57] ABSTRACT

An abrasion evaluation test method is applicable to a case where a rotating disk and a friction member to be brought into sliding contact with the disk contact and abrade each other even while a brake is not applied due to vibrations and mounting errors. The disk is an actual disk, and the friction member is a test piece which is smaller than the actual friction member. The test piece is pressed against a frictional surface of the disk at a predetermined position, thereof. The abrasion of the disk is measured with respect to a portion of the frictional surface that is out of contact with the test piece, while the abrasion of the friction member is obtained from the difference in thickness of the test piece before and after testing.

5 Claims, 2 Drawing Sheets

ABRASION TESTING METHOD

BACKGROUND OF THE INVENTION

1. Field of the Invention

This invention relates to a testing method for evaluating abrasion properties of a friction member in a member such as a brake or a clutch for use in automobiles, industrial vehicles and industrial machines and a mating member with which the friction member is put into sliding contact.

To be more specific, this invention relates to a method of evaluating the abrasion of a disk rotor (hereinafter simply referred to as a disk) resulting from the contact between a pad and the disk of a disk brake while a vehicle equipped with such a disk brake is running and not braked.

2. State of the Prior Art

Various means are known for evaluating the abrasion properties of a friction member such as a pad and a mating member such as a disk. In any of these means, the test is conducted by bringing either a test piece of the mating member and the friction member or an actual mating member and friction member into frictional contact with each other.

A testing machine under JIS D4411 and SAE J661a represents a typical example adopting the former method. As a typical example adopting the latter method, as shown in FIGS. 4 and 5, there is known an inertia type dynamometer having a rotary shaft 1 to which a disk 2 is mounted. Friction members 3 are provided at both sides of the disk 2 to clamp and brake the disk.

The aforementioned testing machines are suitable for the evaluation of the abrasion of a friction member but not for the evaluation of the abrasion of a disk.

The machine under JIS D4411 is adapted to test a disk-shaped mating member. But it is not a disk which is actually used in a disk brake, and it must have a shape peculiar to this machine. Due to this difference in shade between the actually used disk and the disk tested in this machine, the evaluation results will not necessarily reflect the abrasion properties of the actual disk. The machine under SAE J661a uses a drum type mating member, which does not suit the object. Further, no consideration is taken of measurements on the order of microns or measurements of continuous abrasion marks. Thus, no detailed data about the disk are obtainable. Also, the surface pressure applied during the test is 10 kg or more. Testing is impossible at lower pressures.

In the methods in which a disk and a friction member are both tested in the form of test pieces, it is troublesome to cut off such test pieces and fit them on the testing machine, which is one of the factors raising costs. Further, since the test is conducted on a smaller scale, there might be errors in the evaluation results due to the difference in conditions between the actual machine and the testing machine. Thus, such errors have to be corrected. In order to verify the corrected values, a correlation check will be necessary.

On the other hand, the inertia type dynamometer can evaluate the actual abrasion between a disk and a friction member because abrasion is tested between actual examples of both members. But this type of tester is extremely expensive. Further, due to irregular shapes of the friction members, it is necessary for high accuracy to correct the evaluation results of the abrasion of the disk.

The abrasion of the disk due to frictional contact between the disk and the pads while not braked is becoming a big problem, especially in the United States, where automobiles are driven at higher speed and the intervals between brake applications are longer. Namely, due to partial frictional contact between pads and a disk, the disk tends to be abraded locally and its thickness tends to be uneven. When brakes are applied thereafter, the pads which sandwich the disk from both sides will be repeatedly pushed back and forth by the rotating disk due to changes in the thickness thereof, thereby giving the driver extreme uneasiness.

To prevent this, it is essential to find better materials for the disk and the pads. But there has been no suitable evaluation means for determining the quality of the materials. For this purpose, it may be possible to test the abrasion of a disk actually mounted on a car or such tests may be conducted by use of a dynamometer as described above. But the on-the-car test requires that the car be driven 5,000 km or more, and the repeatability is bad. The dynamometer test requires more than 100 hours of testing time, and the repeatability is bad, too.

Further, when evaluating only abrasion, the on-the-car test and the test with a dynamometer pose the following problems.

Pads are usually disposed between the disk and the piston. While braking, they are pressed against the disk. When the brakes are released, the piston retreats slightly. The pads are thus freed between the piston and the disk. But due to vibrations while the car is moving, they will contact the disk. Further, it is impossible to mount the disk perfectly parallel to a pad or the piston. Rather, it tends to be inclined at the rate of about 0.05–0.10 mm/m. Thus, a portion of the disk near each pad will hit the pad once per rotation. The degree of such contact between the disk and the pads varies greatly among different tests depending upon the position of the pads while they are free, dimensions of the disk and the piston, a change in inclination during testing, and the degree of abrasion of the pads. Thus, these tests have a fatal problem in that the characteristics of the pads and the disk are mixed and lost in these many variable factors.

It is an object of this invention to provide an abrasion testing method which is free of these problems.

BRIEF DESCRIPTION OF THE DRAWINGS

Other features and objects of the present invention will become apparent from the following description taken with reference to the accompanying drawings, in which.

DETAILED DESCRIPTION OF THE PREFERRED EMBODIMENT

A first characterizing feature of this invention consists in that an actual disk and a friction member test piece smaller than an actual friction member are used. The test piece is pressed against the frictional surface of the rotating disk on a radially predetermined position thereof at a low surface pressure to abrade the disk and test piece.

Figure 1:
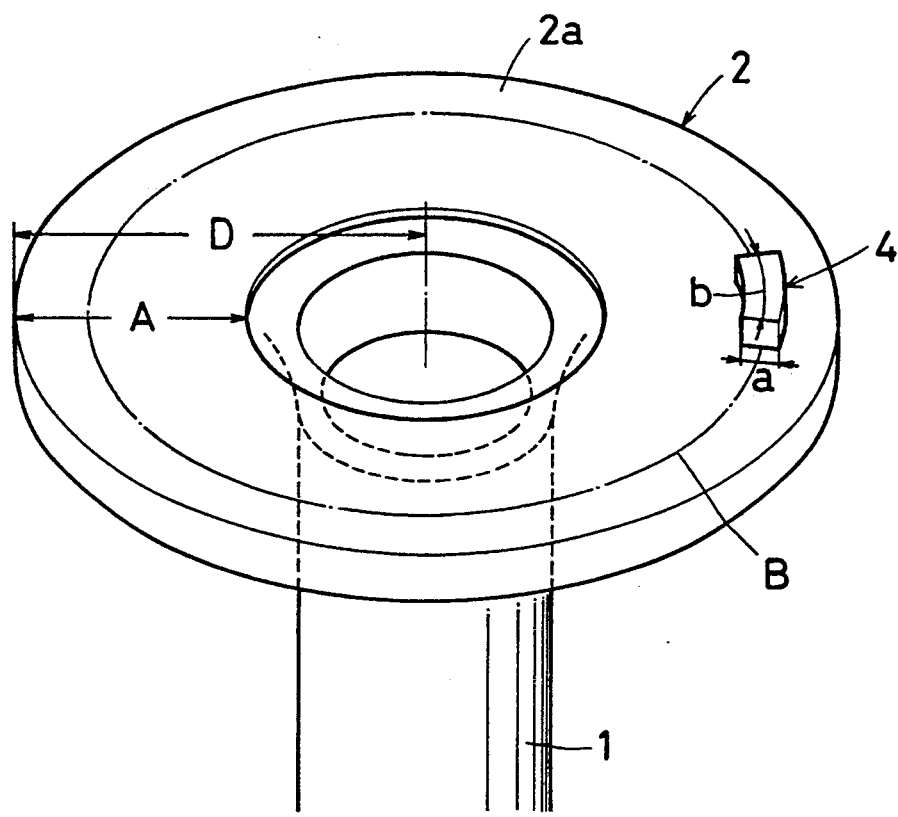
FIG. 1 is a perspective view showing one example of an abrasion testing method according to this invention.

In the example of FIG. 1, an actual disk 2 is set on the top surface of a vertically disposed rotary shaft 1 so that its frictional surface 2a extends horizontally. A test piece 4 cut off from a friction member is placed on the disk so as to be brought into frictional contact with the surface 2a on the radially central portion thereof.

Further, the width a of a contact surface of the test piece (in a diametric direction of the disk), the circumferential length b along the centerline of the contact surface, the width A of the frictional surface the disk and the circumference B of the frictional surface passing the centerline of the test piece are set so as to satisfy the following formula:

$$a = A/15 - A/1.5, \quad b = B/150 - B/15 \text{ and } b > a.$$

The revolving speed of the disk is set at 300–3000 rpm. Abrasion tests are conducted under these conditions with the surface pressure by the test piece set at two different values within a range of not less than a surface pressure due to the weight of the test piece itself and not more than 3 kg/cm$^2$, and the force on the disk (surface pressure multiplied by test piece area) within a range of not more than 10 kg. The results of tests at two different surface pressures are put together for evaluation. This is a second characterizing feature of this invention.

In case of a brake or a friction clutch, it difficult to provide a sufficient gap between a mating member such as a disk and a friction member such as a pad. Rather, they are in light contact with each other in many cases. In such cases, abrasion of the mating member sometimes has a technically large significance. Especially in case of a disk brake, since friction pads and a disk rotor are kept in light contact with each other even while the brake is not applied, the disk rotor might abrade markedly depending upon the materials of these members. Therefore, in selecting the materials, it is important that evaluation tests be conducted under conditions as similar to the actual usage conditions as possible. According to this invention, abrasion tests can be done with no scaledown at the contact portion of the disk with the test piece as compared with an actual device. Also, accurate data on the amount of abrasion and abrasion properties of the frictional surface of the disk with respect to its non-contact portion can be obtained. Further, variable factors of measurement can be eliminated since the evaluation is made at two or more points of surface pressure. Thus, the reliability of the evaluation improves and the optimum materials can be selected or developed.

The abrasion test may be done with different kinds of test pieces set on the same or common position in order to find the best combination of disk material and friction member.

Since the disk used in the test is an actual one, it is necessary only to cut a test piece off a friction member, which can be easily cut. Thus, the test can be done at low cost.

The above-described method has been found to be tile best way to eliminate variable factors present in on-the-car tests or tests using a dynamometer, to lower the cost and to improve the repeatability.

Namely, we found that the frictional contact pressure in this case cannot be kept constant due to the influence of the car body, brakes and disks, that its pressure varies even with the same car and that its absolute value varies from 0 to not more than 3 kg/cm$^2$.

Figure 2:
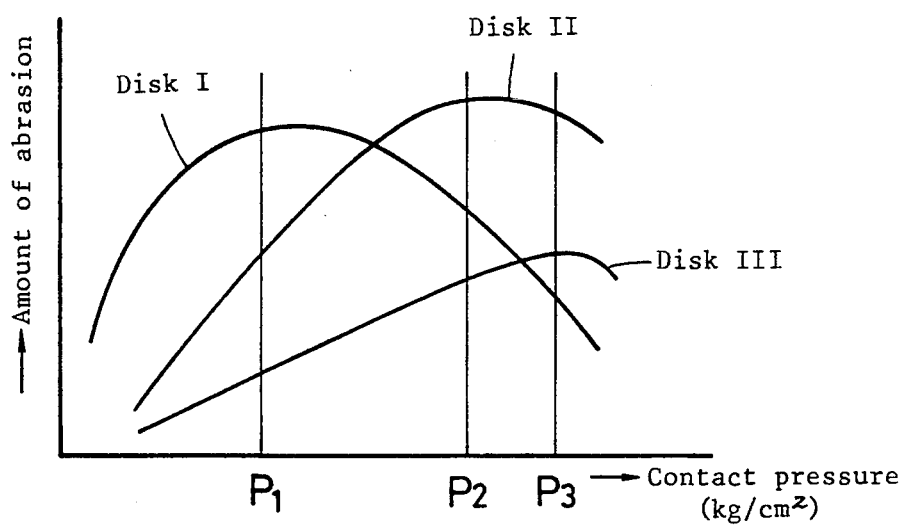
FIG. 2 is a graph showing the relation between the sliding contact pressure and the abrasion of the disk.

On the other hand, it was confirmed that as shown in FIG. 2, the relation between the pressure applied by the pad and the abrasion of the disk depends upon the material of the pad, that the abrasion is not very severe when the revolving speed of the disk is below 300 rpm, and that the pad and the disk are in contact with each other not on the entire contact surface thereof but on a portion covering 1/1.5 or less of the diametric length A of the disk and on the portion covering 1/15 of the circumferential length B of the disk.

Based on these factors, we have found out that tests with good repeatability can be done with a simple tester by using an actual disk and a test piece of a pad which is smaller than the actual size within a necessary range, and that variable factors can be eliminated by evaluating the test results comprehensively with the surface pressures set at two points, so that the characteristics of the disk and the pad can be clarified.

The loading method permits a simple, low-cost and accurate testing by limiting the size of the test piece and the surface pressure and the urging force against the disk. In one method, a weight is placed directly on the test piece. This method is simple, accurate and inexpensive compared to a lever, air or hydraulic method.

In this special application, the surface pressure during a test should not exceed 3 kg/cm$^2$. When the test piece is small and the surface pressure is small, the pressure on the disk is also small. This means that the work volume (proportional to the pressure multiplied by friction coefficient) is small. The smaller the work volume, the smaller the temperature rise due to the frictional heat from the disk. This eliminates the need to cool the disk or can reduce the cooling capacity.

The reason why the test piece should be small compared with the disk, or to put it the other way around, the reason why the disk should be large compared with the test piece, is ease of cooling (higher heat dissipation).

The size a of the test piece should be smaller than the size b because, supposing the revolving speed is the same, the larger the dimension b, the larger the abrasion in the direction of thickness of the disk, thus shortening the testing time. Also, a larger dimension a will cause an unfavorable temperature rise of the disk. The number of revolutions of the disk, which is related to temperature rise, should be not more than 3000 rpm.

Another reason why the test piece should be smaller is because, the larger the dimension a, the more its inner and outer peripheral surfaces will abrade differently because of different sliding speeds between the inner and outer peripheries. Thus, the effect of the surface pressure and that of the sliding speed will get mixed up. Also, a larger dimension b will obscure the effect of the surface pressure because the surface pressure at the leading end thereof with respect to the direction of rotation becomes greater than that at the trailing end thereof. This will lower the evaluation accuracy. But too small a test piece size will make the test difficult. Thus, the dimensions a and b have their lower limits.

The test should be conducted for two or more different surface pressure points. For example, in FIG. 2, if the evaluation is made at pressure P1 only, the abrasion of three kinds of disk I, II and III will be judged as I>II>III; if made at pressure P2 only, they will be II>I>III; and if made at pressure P3 only, they will be II>III>I. Thus, it is not clear which one of the disks is the most resistant to abrasion. But the results of tests conducted for individual pressures P1, P2 and P3 will reveal that the disk III is superior to the disks I and II. This is because, as described above, the contact pressure acts on disks at random when the friction member is actually mounted on a car.

According to the above-described methods, test pieces having a predetermined shape can be cut off from friction members having different shapes, so that the characteristics of different friction members can be compared.

By setting the test pieces on a common position (by making uniform the distance D from the center of potation in FIG. 1), the characteristics of disks made of different materials or having different dimensions or shapes can be compared.

Figure 3:
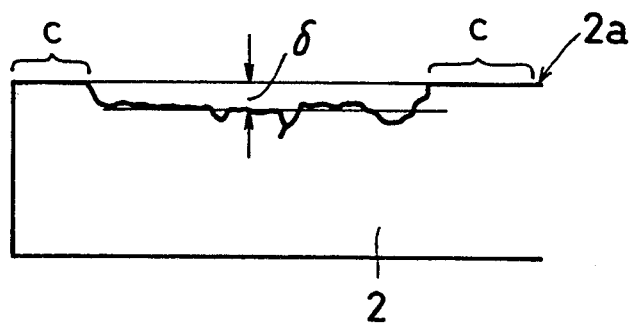
FIG. 3 is a sectional view showing the average abrasion on the frictional surface of a disk as compared with the non-worn surface.
Figure 4:
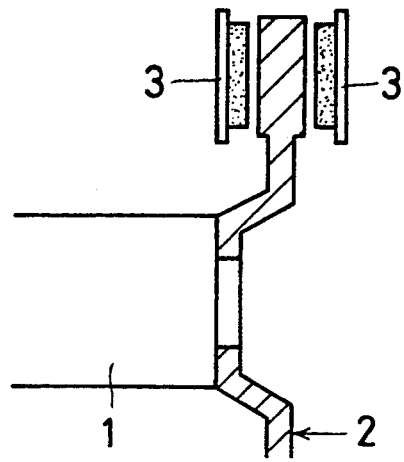
FIG. 4 is a sectional view showing an abrasion testing method using an inertia type dynamometer.
Figure 5:
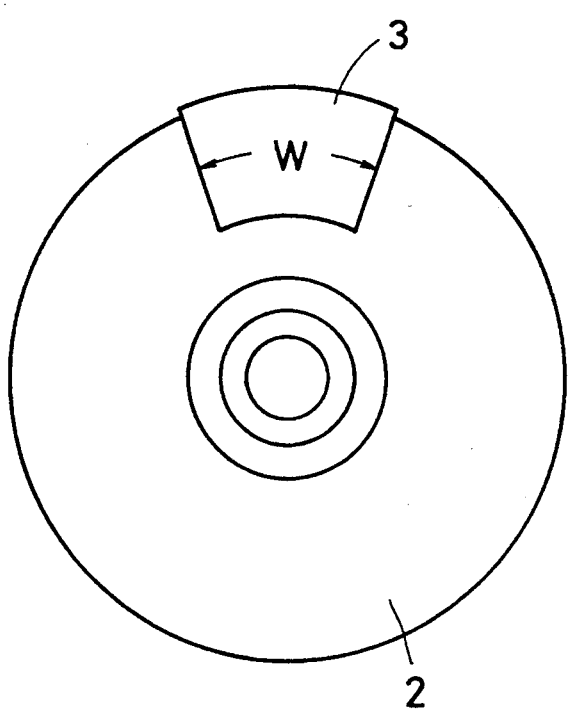
FIG. 5 is an end view showing the method of FIG. 4.

Further, since the dimension a of the test piece 4 is smaller than the width A of the frictional surface on the disk, as shown in FIG. 3, the surface roughness of the worn surface and the average abrasion amount can be measured with reference to the non-contact portion of the test piece (C in FIG. 3) where the surface is not worn. Thus, precise and detailed data can be obtained. As to the accuracy in evaluation of the disk, since the disk 2 is a real disk, e.g. a disk rotor itself of a disk brake, and the only difference at the contact portion with the test piece is that the dimension b of the test piece 4 in the direction of rotation of the disk is small compared with the dimension W in FIG. 5, Then there is no scale-down and little difference from the real article at this portion. Further, since the evaluation is carried out at two or more points for general evaluation, variable factors can be eliminated. This serves to improve the reliability of the evaluation.

What is claimed is:

1. A testing method for evaluating the abrasion of rotating disks and friction members of brakes, wherein a friction member and a respective rotating disk of a brake contact each other and abrade while the brake is not applied due to vibrations and mounting errors, said testing method comprising the steps of:

pressing a test piece friction member, which is smaller than an actual friction member, against a portion of a frictional surface of an actual disk at a predetermined position, maintaining a portion of the frictional surface out of contact with the test piece friction member and rotating the test piece friction member and the actual disk relative to each other;

measuring the degree of abrasion of the disk with respect to the portion of the frictional surface maintained out of contact with the test piece friction member; and obtaining the degree of abrasion of the test piece friction member by determining the difference in the thickness of said test piece friction member before and after said step of pressing.

2. The testing method of claim 1, wherein the test piece friction member has a contact surface having a width a and a centerline of a length b that extends in a circumferential direction of the disk in said step of pressing;

the frictional surface of the disk has a width A and a circumference B at the centerline of the contact surface of the test piece friction member in said step of pressing;

during said step of pressing, $$a = A/15 - A/1.5,\ b = B/150 - B/15\ \text{and}\ b > a,$$

and the disk is rotated at a revolving speed of 300–3000 rpm;

said steps of pressing, measuring and obtaining are conducted for two different values of the surface pressure of the test piece friction member on the disk, the two different values being within a range of at least the surface pressure due to the weight of the test piece friction member by itself and at most 3 kg/cm$^2$, the surface pressure multiplied by the area of the contact surface of the test piece friction member being at most 10 kg; and the results from conducting said steps of pressing, measuring and obtaining for the two different values of the surface pressure are evaluated together.

3. A testing method for evaluating the abrasion of rotating disks of brakes having rotating disks and friction members for frictional contact with the rotating disks, said testing method comprising the steps of:

pressing a test piece friction member, which is a test piece smaller than an actual one of the friction members, against a portion of a frictional surface of an actual one of the rotating disks at a predetermined position, maintaining a portion of the frictional surface out of contact with the test piece friction member and rotating the test piece friction member and the actual disk relative to each other; and measuring the degree of abrasion of the disk with respect to the portion of the frictional surface maintained out of contact with the test piece friction member.

4. The testing method of claim 3, wherein:

the test piece friction member has a contact surface having a width a and a centerline of a length b that extends in a circumferential direction of the disk in said step of pressing;

the frictional surface of the disk has a width A and a circumference B at the centerline of the contact surface of the test piece friction member in said step of pressing; and during said step of pressing, $$a = A/15 - A/1.5,\ b = B/150 - B/15\ \text{and}\ b > a,$$

and the disk is rotated at a revolving speed of 300–3000 rpm.

5. The testing method of claim 4, wherein:

said steps of pressing, measuring and obtaining are conducted for two different values of the surface pressure of the test piece friction member on the disk, the two different values being within a range of at least the surface pressure due to the weight of the test piece friction member by itself and at most 3 kg/cm$^2$, the surface pressure multiplied by the area of the contact surface of the test piece friction member being at most 10 kg.

* * * * *